United States Patent [19]

Ciganek

[11] Patent Number: 4,767,764
[45] Date of Patent: Aug. 30, 1988

[54] ALKOXYALKYL AND ALKYLMERCAPTOALKYL SUBSTITUTED BRIDGED BENZOFUROISOQUINOLINES HAVING OPIOID ANTAGONIST AND/OR APPETITE-CONTROLLING PROPERTIES

[75] Inventor: Engelbert Ciganek, Kennett Square, Pa.

[73] Assignee: E. I. Du Pont de Nemours and Company, Wilmington, Del.

[21] Appl. No.: 867,157

[22] Filed: May 27, 1986

[51] Int. Cl.$^4$ .................... A61K 31/47; C07D 491/08
[52] U.S. Cl. ........................... 514/282; 544/44; 544/46
[58] Field of Search ............. 546/44, 46; 514/282

[56] References Cited

U.S. PATENT DOCUMENTS 4,477,456 10/1984 Ciganek .................... 514/282

FOREIGN PATENT DOCUMENTS 0070427 1/1983 European Pat. Off. ............ 546/44
0164136 12/1985 European Pat. Off. ............ 546/46

Primary Examiner—Donald G. Daus
Assistant Examiner—Diana G. Rivers

[57] ABSTRACT

Alkoxyalkyl and alkylmercaptoalkyl substituted bridged benzofuroisoquinolines have opioid antagonist, and/or appetite-controlling properties. Preferred compounds are kappa receptor selective antagonists. Examples of such preferred compounds are 5-Methoxymethyl-3-n-propyl-1,2,3,4,5,6,7,7a-octahydro-4a,7-ethanobenzofuro[3,2-e]isoquinolin-9-ol and 3-Cyclopropylmethyl-5-methoxymethyl-1,2,3,4,5,6,7,7a-octahydro-4a,7-ethanobenzofuro[3,2-e]isoquinoline-9-ol.

39 Claims, No Drawings

ALKOXYALKYL AND ALKYLMERCAPTOALKYL SUBSTITUTED BRIDGED BENZOFUROISOQUINOLINES HAVING OPIOID ANTAGONIST AND/OR APPETITE-CONTROLLING PROPERTIES

FIELD OF THE INVENTION

This invention relates to bridged benzofuroisoquinolines, processes for their manufacture, and their use as opioid antagonists and as appetite-controlling agents.

BACKGROUND OF THE INVENTION

Studies of the binding properties of opioid drugs and peptides at specific sites in the brain and other organs have suggested the existence of several types of opioid receptors. In the central nervous system (CNS), good evidence has been demonstrated for at least three categories of opioid receptors: $\mu$ (mu), $\kappa$ (kappa) and $\delta$ (delta). The established opioid antagonists naloxone and naltrexone bind to all three types of receptors, with greatest affinity for the mu receptor.

The mu receptor is thought to mediate several components of opioid drug effects including supraspinal analgesia, respiratory depression, euphoria, and physical dependence. Because of their strong mu antagonist activity, naloxone type antagonists are used for the treatment of opioid overdose toxicity (especially respiratory depression), the diagnosis of opioid dependence, and for the treatment of opioid addiction.

Naloxone type antagonists also have demonstrated effects in testing symptoms not specifically related to mu agonist activity. Naloxone has been shown to improve hemodynamic parameters in a variety of animal models of hemorrhagic, septic, and neurogenic shock. In these models, however, effective doses of naloxone are several orders of magnitude higher than doses useful in reversing mu mediated effects, suggesting that the opioid antagonist effectiveness of naloxone is being mediated through other opioid receptor systems (kappa, delta, etc.). Additionally, naloxone type antagonists often have limited effectiveness in these systems. Dose-response curves may plateau at less than 100% effectiveness or even show loss of effectiveness at higher doses (inverted U-shaped dose response curves), possible indicators of partial or counteracting activities. The involvement of kappa mediation in these systems has been suggested in several studies. In spinal trauma or ischemia, the prototypical kappa agonist opioid peptide dynorphin has been implicated as a major factor in the development of neurologic pathophysiology (Holaday, J. W., Faden, A. I., "Naloxone Acts at Central Opiate Receptors to Reverse Hypotension, Hypothermia, and Hypoventilation in Spinal Shock", *Brain Research,* 189, 295-299, 1980). In animal studies of spinal cord injury using a "spinal stroke" model in the rabbit, naloxone was less effective than WIN 44,441-3 (an opioid antagonist with enhanced activity at the kappa receptor), suggesting that kappa antagonist properties may be of greater importance than mu antagonist activity in the therapeutic effectiveness of antagonists in these systems (Faden, A. I., Jacobs, T. P., "Opiate Antagonist WIN 44,441-3 Stereospecifically Improves Neurologic Recovery After Ischemic Spinal Injury", *Neurology,* 35, 1311-1315, 1985).

Another serious problem for which help is often sought is obesity. It can lead to a number of serious side-effects, not the least of which is an increased risk of cardiovascular disease. A number of appetite suppressants are currently available for the treatment of obesity, but none is completely satisfactory.

Several animal studies have suggested a role of the opioid system in the control of food intake. Kappa agonist agents such as ethylketocyclazocine and U-50,488H have been shown to be more potent stimulators of feeding than the mu agonist morphine (Morley, J. E., Levine, A. S., Grace M., Kneip, J., "An Investigation into the Role of Kappa Opiate Receptor Agonists in the Initiation of Feeding", *Life Sci.,* 31, 2617, 1982.) Autoradiographic studies have shown that high densities of kappa receptors are found localized within specific brain areas known to regulate ingestive behaviors (Lynch, W. C., Watt, J., Krall, S., Paden, C. M., "Autoradiographic Localization of Kappa Opiate Receptors in CNS Taste and Feeding Areas", *Pharmacology, Biochemistry & Behavior,* 22, 699-705, 1985). Naloxone and naltrexone have been shown to decrease food intake in several animal species, but here again the effective doses are much larger than those useful in reversing mu mediated effects. Thus, a more selective kappa antagonist could possibly have a greater degree of therapeutic effectiveness than naloxone and naltrexone in decreasing food intake behavior.

Kappa selective opioid antagonists have demonstrated some improved utility in treatment of shock, stroke, and the control of food intake. Other suggested therapeutic utilities for the kappa selective antagonists include modulation of endocrine dysfunctions since kappa receptors have shown effects in mediating endocrine function.

Thus, it would be highly desirable to obtain a compound which has a significant degree of selectivity for the kappa receptor, allowing antagonist effects to be achieved at doses not complicated by mu antagonist effects or by effects not mediated through opioid receptors. A selective kappa antagonist may provide an agent which is more fully effective than a non-selective antagonist in those conditions (shock, stroke, obesity, endocrine dysfunction) whose etiology appears related to kappa function.

E. Ciganek, U.S. Pat. No. 4,477,456, describes compounds of the classes, 1,2,3,4,5,6,7,7a-octahydro-4a,7-ethanobenzofuro[3,2-e]isoquinolines and 1,2,3,4,5,6,7,7a-octahydro-4a,7-ethenobenzofuro[3,2-e]isoquinolines that exhibit analgesic, narcotic antagonist, mixed analgesic/narcotic antagonist, and/or anorexigenic properties. These compounds have Formula (I):

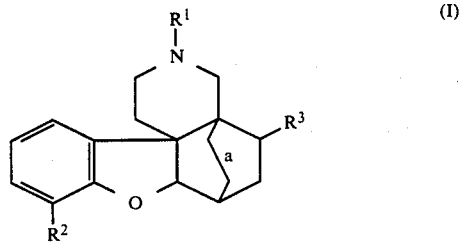

wherein:
$R^1$ is H, $C_1$-$C_{10}$ alkyl, $CH_2$—$R^6$, $C_2H_4(C_6H_4)R^7$, or $(CH_2)_nCN$, in which $n=1$-3;
$R^2$ is H, OH, $C_1$-$C_2$ alkoxy, or $C_2$-$C_{12}$ acyloxy of an alkanoic acid;

$R^3$ is H, $C_1$–$C_8$ alkyl, or $C(OH)(R^5)$;
a is a single bond or a double bond;
$R^4$ is H or $C_1$–$C_8$ alkyl;
$R^5$ is H, $C_1$–$C_8$ alkyl, $C_2$–$C_8$ alkenyl, $C_3$–$C_8$ cycloalkyl, or $(CH_2)_m$—$C_6H_5$ in which m=0–4;
$R^6$ is $CH{=}C(R^8)(R^9)$, $C{\equiv}CH$, $C_3$–$C_6$ cycloalkyl, phenyl, 2-thienyl, 2-furyl, 2-tetrahydrofuryl, methyl substituted 2-tetrahydrofuryl;
$R^7$ is H, $C_1$–$C_3$ alkyl, $OCH_3$, Cl, Br, or F; and
$R^8$ and $R^9$ are independently H, $CH_3$, or Cl.

A coassigned, pending application U.S. Ser. No. 774,025, filed Sept. 9, 1985, discloses a process for preparing compounds of Formula (I) and intermediates thereof.

SUMMARY OF THE INVENTION

According to the present invention there is provided a compound having the formula:

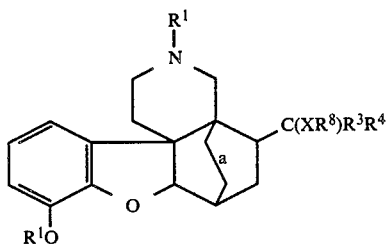

(II)

or an acid addition salt thereof, wherein
a is a single or double bond;
$R^1$ is n-propyl or $CH_2R^5$;
$R^2$ is H, alkyl of 1–2 carbons, $C_{2-12}$ acyl of an alkanoic acid, or

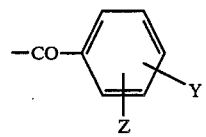

$R^3$ is H or alkyl of 1–8 carbons;
$R^4$ is H, alkyl of 1–8 carbons; alkenyl of 1–8 carbons, cycloalkyl of 3–8 carbons, or $(CH_2)_m C_6H_5$ in which m is 0–4 inclusive;
$R^5$ is $CH{=}C(R^6)(R^7)$, $C{\equiv}CH$, or cyclopropyl provided that when $R^5$ is cyclopropyl, then $R^2$, $R^3$ and $R^4$ are independently H and $R^8$ is $CH_3$ or $(CH_2)_n C_6H_5$ in which n is 3–4 inclusive;
$R^6$ and $R^7$ independently are H, $CH_3$ or Cl;
$R^8$ is alkyl of 1–8 carbons, alkenyl of 1–8 carbons, cycloalkyl of 3–8 carbons, or $(CH_2)_n C_6H_5$ in which n is 3–4 inclusive;
X is O or S;
Y and Z independently are H, $OR^9$, $NHR^9$, or $NR^9R^{10}$, provided at least one of Y or Z is $OR^9$, $NHR^9$, or $NR^9R^{10}$;
$R^9$ is H, alkyl of 1–4 carbons, or $COR^{11}$;
$R^{10}$ is alkyl of 1–4 carbons, or $COR^{11}$; and
$R^{11}$ is H or alkyl of 1–4 carbons.

Also provided is an N-oxide derivative of a compound of Formula (II).

Further provided is a pharmaceutical composition comprising at least one of the above-described compounds and a pharmaceutical carrier.

Additionally provided is a method for alleviating the effect of an opioid drug and/or exerting an appetite-controlling effect in a mammal, comprising administering to the mammal an effective antagonist or appetite-controlling amount of at least one of the above-described compounds.

It is intended that the compounds of above Formula (II) include within its description the racemates and the dextro- and levorotatory antipodes thereof, and pharmaceutically suitable acid addition salts thereof.

DESCRIPTION OF THE INVENTION

Preferred compounds are those compounds of Formula (II) where:
(a) $R^1$ is n-propyl or cyclopropylmethyl, provided that when $R^1$ is cyclopropylmethyl, then $R^2$, $R^3$ and $R^4$ are H, and $R^8$ is $CH_3$ or $(CH_2)_n C_6H_5$ in which n is 3–4; or
(b) $R^2$ is H; or
(c) $R^3$ and $R^4$ are H; or
(d) $R^8$ is alkyl of 1–3 carbons; or
(e) X is O; or
(f) a is a single bond.

Especially preferred compounds are those compounds of Formula (II) that are pure antagonists. These are compounds where:
(a) $R^1$ is n-propyl or cyclopropylmethyl;
(b) $R^2$, $R^3$ and $R^4$ are H;
(c) $R^8$ is alkyl of 1–3 carbons; and
(d) a is a single bond.

Of these pure antagonist compounds, those where $R^1$ is n-propyl are particularly preferred.

Specifically preferred compounds are:
(a) 5-Methoxymethyl-3-n-propyl-1,2,3,4,5,6,7,7a-octahydro-4a,7-ethanobenzofuro[3,2-e]isoquinolin-9-ol; and
(b) 3-Cyclopropylmethyl-5-methoxymethyl-1,2,3,4,5,6,7,7a-octahydro-4a,7-ethanobenzofuro[3,2-e]-isoquinolin-9-ol.

The compounds of the invention can be prepared by procedures such as those illustrated below.

The following equations illustrate reactions useful in the preparation of compounds of the invention:

SCHEME 1

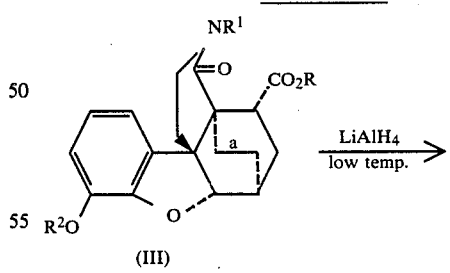

(III)

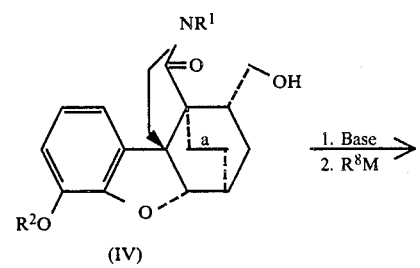

(IV)

-continued
SCHEME 1

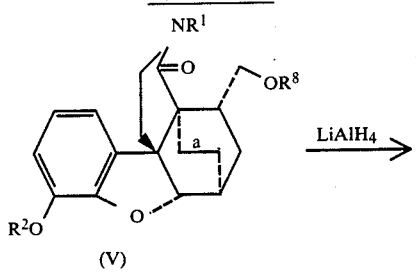

(V)

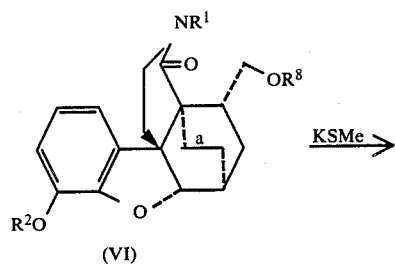

(VI)

Compounds of Formula (III) are disclosed in U.S. Pat. No. 4,477,456. Selective reduction of the ester function of compounds of Formula (III), with a reducing agent such as lithium aluminum hydride at −20° to +10° C., or other hydride reducing agents that reduce esters but not lactams, gives the primary alcohols of Formula (IV). These are converted into the ethers of Formula (V) by treating with a suitable base such as potassium or sodium hydride, or sodamide, in a non-hydroxylic solvent such as tetrahydrofuran, diethyl ether, or dimethylformamide at a temperature in the range of 0°–100° C. and reacting the resultant alcoholate with an alkylating agent $R^8M$, where M is a good leaving group such as Cl, Br, I, $OSO_2Me$, or $OSO_2Ar$ (Ar=an aromatic moiety) at a temperature in the range of 0°–100° C. The lactam function in the ether of Formula (V) is then reduced, with a reducing agent such as lithium aluminum hydride in tetrahydrofuran at its boiling point (67° C.) or with borane or borane-methyl sulfide, when a is a single bond, under similar conditions. The phenol ether of Formula (VI) may then be converted into a phenol of Formula (VII) by standard methods such as treatment with an alkyl metal mercaptide in dimethylformamide at a temperature in the range of 100°–200° C. This process provides compounds of the invention where $R^3$ and $R^4$ are H, X is oxygen and a is a single or double bond.

The process of Scheme 1 is illustrated by Examples 1 (method A), 2 and 7. In Example 7, the alkylating agent $R^8M$ is cinnamyl bromide ($BrCH_2CH=CHC_6H_5$). Hydrogenation of the double bond gives the 3-phenylpropyl derivative.

SCHEME 2

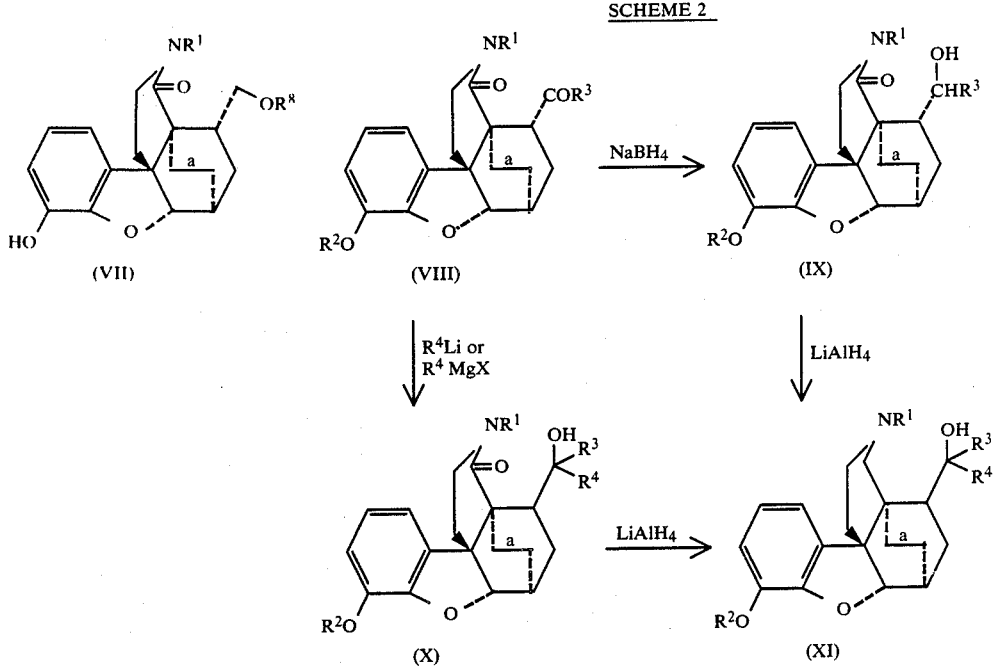

A compound of Formula (VIII), disclosed in the U.S. Pat. No. 4,477,456, can be reduced selectively with lithium aluminum hydride at a low temperature as in Scheme 1; or, preferably, with sodium borohydride in an alcoholic solvent such as ethanol, or lithium borohydride in an ethereal solvent such as tetrahydrofuran, at a temperature in the range of −50° to +30° C., to give a secondary alcohol of Formula (IX). Treatment of a compound of Formula (VIII) with alkyllithium reagents, or Grignard reagents, in an ethereal solvent such as tetrahydrofuran at a temperature in the range of −50° to +30° C., gives a tertiary alcohol of Formula (X). Compounds of Formulas (IX) and (X) are then treated as in Scheme 1 to give compounds of Formula (XI) where $R^4$ is H and $R^3$ is not H or where neither $R^3$ nor $R^4$ is H; a can be either a single or a double bond.

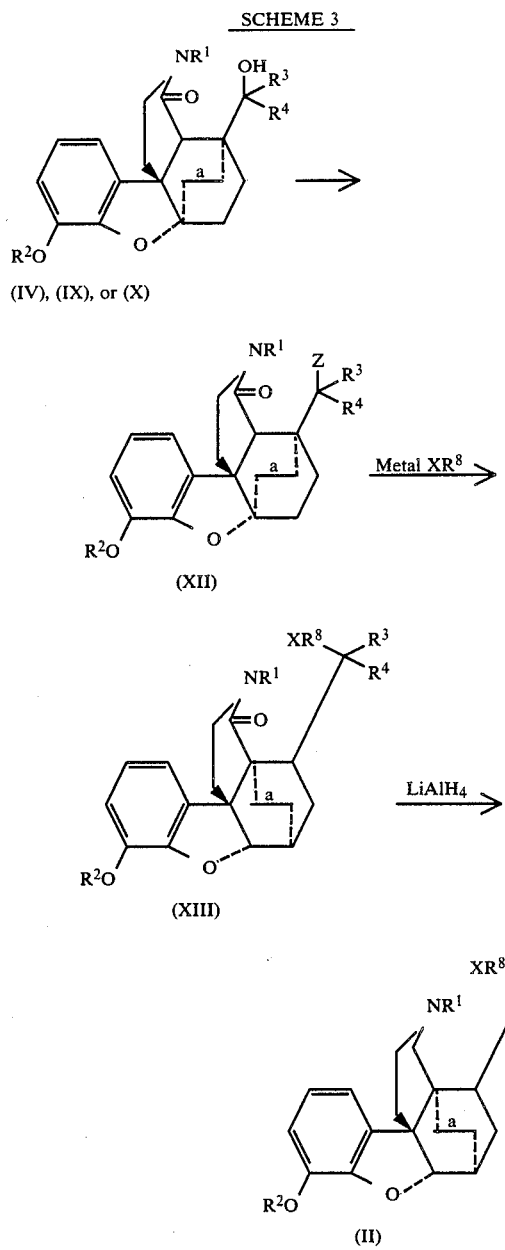

a single or double bond. This reaction is exemplified by Example 5.

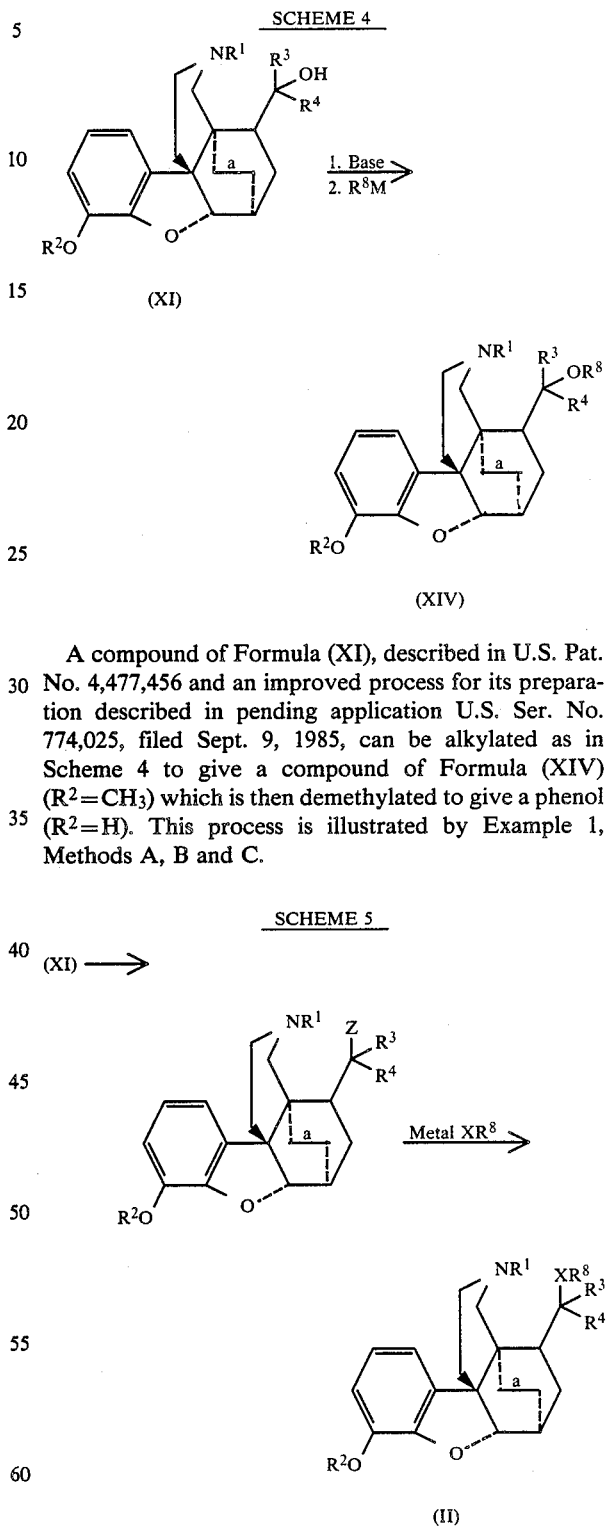

A compound of Formula (XI), described in U.S. Pat. No. 4,477,456 and an improved process for its preparation described in pending application U.S. Ser. No. 774,025, filed Sept. 9, 1985, can be alkylated as in Scheme 4 to give a compound of Formula (XIV) ($R^2 = CH_3$) which is then demethylated to give a phenol ($R^2 = H$). This process is illustrated by Example 1, Methods A, B and C.

The hydroxyl group in an alcohol of Formula (IV), (IX), or (X) is activated by formation of an ester such as with methanesulfonic acid or toluenesulfonic acid ($Z = OSO_2Me$ or $OSO_2C_6H_4Me$) or conversion into a halide ($Z = Br$ or $I$) by known methods. The intermediate of Formula (XII) is then treated with a metal alcoholate or metal mercaptide, preferably in an ethereal solvent such as tetrahydrofuran, or in dimethyl formamide at temperatures in the range of 0° to 150° C. to give an ether or thioether of Formula (XIII). The lactam compound of Formula (XIII) is then reduced as in Scheme 1 to give a compound of the invention; a can be Scheme 5 illustrates a variation of Scheme 3 where the substrate for the introduction of the $XR^8$ group is an amine of Formula (XI) instead of a lactam of Formula (IV), (IX), or (X). The process of this conversion is illustrated by Examples 3 and 4.

SCHEME 6

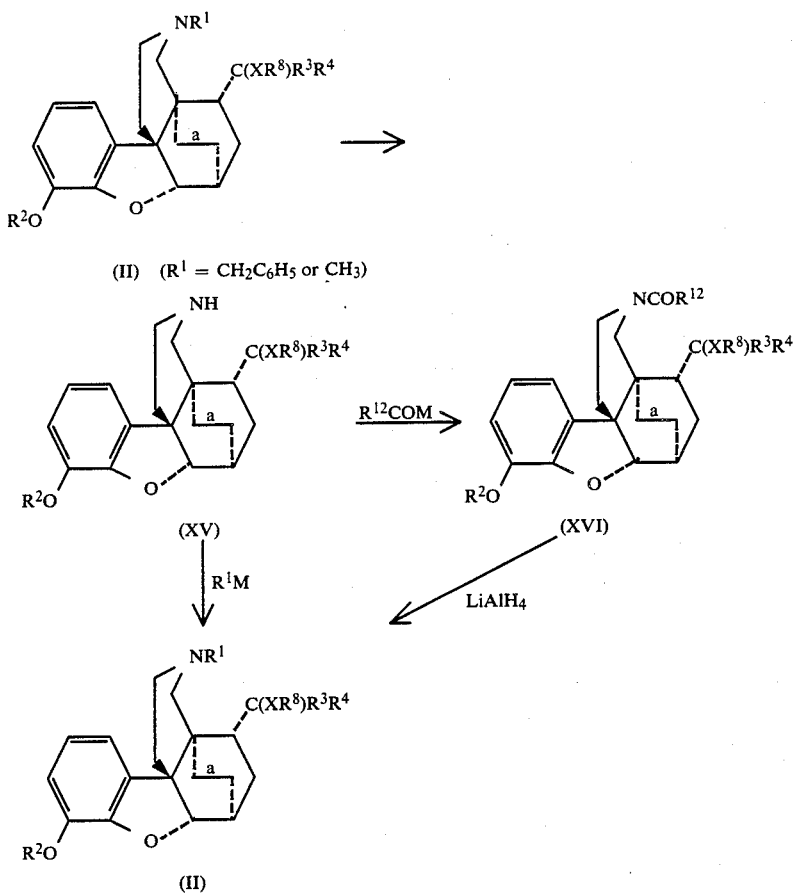

The group $R^1$ can be introduced in the beginning of the synthesis as shown in Schemes 1-5. Alternatively (Scheme 6), an easily removable group $R^1$ can be used temporarily (such as a benzyl or a methyl group) and can then be removed later in the process by methods known to one skilled in the art such as catalytic hydrogenation (when a is a single bond), treatment with cyanogen bromide (von Braun reaction) or reaction with an alkyl chloroformate. The desired group $R^1$ is then introduced by direct alkylation with an alkylating agent $R^1M$ where M is a good leaving group, such as Br or I, in a solvent, preferably having a high dielectric constant, such as dimethylformamide, at a temperature in the range of 0° to 150° C., in the presence of a base, preferably an alkali metal carbonate. This variation is exemplified by Example 1, Method B.

For certain $R^1$ groups where the functional group directly attached to nitrogen is methylene, the secondary amine of Formula (XV) can be acylated with an acyl chloride or acyl bromide, preferably in a two phase system such as methylene chloride-water, in the presence of a base such as sodium hydroxide at a temperature in the range of −20° to 50° C. Alternatively, the reaction can be run in a non-hydroxylic solvent such as an ether or methylene chloride in the presence of an organic base such as pyridine. The amides (XVI) so obtained are then reduced to the amines (II) with lithium aluminum hydride or similar metal hydrides in a solvent such as tetrahydrofuran. This process for introducing $R^1$ is illustrated by Example 1 (Method C).

The preferred group $R^2$ in all intermediates in Schemes 1-6 is $CH_3$.

The compounds of the invention, their use and the processes for making them will be better understood by reference to the following illustrative examples, in which all indications of percentage are by weight unless otherwise indicated and temperatures are in degrees Celsius.

In these compounds, d and l optical isomers occur as racemic mixtures which can be resolved by known methods (e.g. Eliel, *Stereochemistry of Carbon Compounds*, McGraw-Hill, 1962 page 21). The optical isomers corresponding to the absolute configuration of morphine are preferred.

EXAMPLE 1

5-Methoxymethyl-3-n-propyl-1,2,3,4,5,6,7,7a-octahydro-4a,7-ethanobenzofuro[3,2-e]isoquinolin-9-ol
($R^1=CH_2CH_2CH_3$; $R^2$, $R^3$, $R^4=H$; $R^8=CH_3$; $X=O$; a=single bond)

Method A
9-Methoxy-3-n-propyl-2,3-dihydro-1H-benzofuro[3,2-e]isoquinolin-4[7aH]-one, m.p. 126°-128°, was prepared according to the procedures given in U.S. Pat. No. 4,243,668 and subjected to a Diels-Alder reaction with methyl acrylate as described for the 3-cyclopropylmethyl analogue in U.S. Pat. No. 4,477,456. Crystallization from ethyl acetate gave the pure major isomer of 9-methoxy-3-n-propyl-5-methoxycarbonyl-1,2,5,6,7,7a-hexahydro-4a,7-ethenobenzofuro[3,2- e]isoquinolin-4(3H)-one in 60% yield, m.p. 158°–160°. Catalytic hydroxygenation of this product using the procedure described in U.S. Pat. No. 4,477,456 gave 9-methoxy-3-n-propyl-5-methoxycarbonyl-1,2,5,6,7,7a-hexahydro-4a,7-ethanobenzofuro[3,2-e]isoquinolin-4(3H)-one; NMR spectrum ($\delta$ in CDCl$_3$); 6.8 (m, 2H); 6.5 (d/d, 1H); 4.5 (s, 1H); 3.9 (s, 3H); 3.7 (s, 3H) and 1.0 (t, 3H), among others.

To a solution of 7.37 g of 9-methoxy-3-n-propyl-5-methoxycarbonyl-1,2,5,6,7,7a-hexahydro-4a,7-enthanobenzofuro[3,2-e]isoquinolin-4(3H)-one in 50 ml of tetrahydrofuran was added, with ice cooling, 30 mL of a 1M solution of lithium aluminum hydride in tetrahydrofuran. The mixture was stirred in an ice bath for 45 minutes, and the excess hydride was decomposed by sequential addition of 1.1 mL of water, 1.1 mL of 15% aqueous sodium hydroxide, and 3.3 mL of water. Removal of the solvent from the filtered mixture gave 6.41 g of 5-hydroxymethyl-9-methoxy-3-n-propyl-1,2,5,6,7,7a-hexahydro-4a,7-ethanobenzofuro[3,2-e]isoquinolin-4(3H)-one; NMR spectrum ($\delta$ in CDCl$_3$); 6.8 (m, 2H); 6.5 (d/d, 1H); 4.5 (s, 1H); 3.9 (m+s, 4H) and 1.0 (t, 3H), among others.

To a mixture of 9 g of 35% potassium hydride in oil, prewashed with hexane, and 40 mL of tetrahydrofuran was added 4.05 g of 5-hydroxymethyl-9-methoxy-3-n-propyl-1,2,5,6,7,7a-hexahydro-4a,7-ethanobenzofuro[3,2-e]isoquinolin-4(3H)-one. The mixture was stirred at room temperature for 30 minutes, and then heated under reflux for 30 minutes. Methyl iodide (8 mL) was added to the cooled mixture which was then heated under reflux for one hour. Excess hydride was destroyed by addition of 10 mL of methanol, and the solvent was removed. The product was taken up in methylene chloride/water, and the aqueous layer was extracted with methylene chloride. Removal of the solvent gave 4.45 g of 9-methoxy-5-methoxymethyl-3-n-propyl-1,2,5,6,7,7a-hexahydro-4a,7-ethanobenzofuro[3,2-e]isoquinolin-4(3H)-one. NMR spectrum ($\delta$ in CDCl$_3$); 6.8 (m, 2H); 6.5 (m, 1H); 4.5 (s, 1H); 3.9 (s, 3H); 3.3 (s, 3H) and 1.0 (t, 3H), among others.

A mixture of the above product and 50 mL of a 1M solution of lithium aluminum hydride in tetrahydrofuran was heated under reflux for 16 hours. Workup as described above and short-path distillation of the product (180° bath temperature, 1 micron) gave 3.85 g of 9-methoxy-5-methoxymethyl-3-n-propyl-1,2,3,4,5,6,7,7a-octahydro-4a,7-ethanobenzofuro[3,2-e]isoquinoline. NMR spectrum ($\delta$ in CDCl$_3$): 7.3 (m, 1 H); 6.8 (m, 2H); 4.4 (s, 1H); 3.9 (s, 3H), 3.4 (s, 3H) and 1.0(t, 3H), among others. Mass spectrum; m/e calcd. for C$_{23}$H$_{33}$NO$_3$; 371.2460; measured: 371.2406.

A mixture of the above product, 4 g of potassium methyl mercaptide and 50 mL of dry dimethylformamide was stirred under nitrogen in an 140° oil bath for 6 hours. The cooled mixture was acidified with conc. hydrochloric acid, and the solvents were removed under vacuum. The residue was stirred with aqueous ammonium hydroxide solution and methylene chloride, and the aqueous phase was extracted repeatedly with methylene chloride. Removal of the solvent and crystallization of the residue from ethyl acetate gave 2.0 g of 5-methoxymethyl-3-n-propyl-1,2,3,4,5,6,7,7a-octahydro-4a,7-ethanobenzofuro[3,2-e]isoquinolin-9-ol, m.p. 130°–131°. NMR spectrum ($\delta$ in CDCl$_3$); 7.15 (d, J=8 Hz, 1H); 6.80 (d, J=8 Hz, 1H); 6.70 (t, J=8 Hz, 1H); 4.35 (narrow multiplet, 1H); 3.50 (d/d, J=9/5 Hz, 1H); 3.35 (s, 3H); 3.30 (t, J=9 Hz, 1H); and 0.95 (t, 3H), among others.

Method B

To a suspension of 12.7 g of 35% potassium hydride in oil, prewashed with hexane, in 100 mL of tetrahydrofuran was added 9.8 g of 3-benzyl-5-hydroxymethyl-9-methoxy-1,2,3,4,5,6,7,7a-octahydro-4a,7-ethenobenzofuro[3,2-e]isoquinoline (E. Ciganek and B. K. Wong, coassigned pending application, U.S. Ser. No. 774,025) and the mixture was heated under reflux for 4 hours. Methyl iodide (5.2 g) was added with cooling, and the mixture was stirred at room temperature for 18 hours. Addition of water and extraction with methylene chloride gave 10.36 g of 3-benzyl-5-methoxymethyl-9-methoxy-1,2,3,4,5,6,7,7a-octahydro-4a,7-ethenobenzofuro[3,2-e]isoquinoline. NMR spectrum ($\delta$ in CDCl$_3$); 7.5–7.2 (m, 5H); 7.2 (m, 1H); 6.7 (m, 2H); 6.1 (d/d, 1H); 5.5 (d, 1H); 4.4 (s, 1H); 3.9 (s, 3H); 3.8 (d, J=13 Hz, 1H); 3.6 (d, J=13 Hz, 1H); and 3.2 (s, 3H), among others.

Catalytic hydrogenation of the above product in glacial acetic acid and a 10% palladium on carbon catalyst for one week at room temperature gave 8.14 g of 5-methoxymethyl-9-methoxy-1,2,3,4,5,6,7,7a-octahydro-4a,7-ethanobenzofuro[3,2-e]isoquinoline. NMR ($\delta$ in CDCl$_3$); 7.3 (m, 1H); 6.8 (m, 2H); 4.4 (m, 1H); 3.9 (s, 3H) and 3.4 (s, 3H), among others.

The above product was stirred with 80 mL of dimethylformamide, 4.26 g of 1-bromopropane and 5.1 g of sodium carbonate at room temperature for 20 hours. Removal of the solvent, workup with water and methylene chloride; and short-path distillation (245° bath temperature, 2 micron) gave 7.47 g of 9-methoxy-5-methoxymethyl-3-n-propyl-1,2,3,4,5,6,7,7a-octahydro-4a,7-ethanobenzofuro[3,2-e]isoquinoline whose NMR spectrum was identical to that of the same product obtained by Method A. Demethylation as described in Method A gave 5-methoxymethyl-3-n-propyl-1,2,3,4,5,6,7,7a-octahydro4a,7-ethanobenzofuro-[3,2-e]isoquinolin-9-ol, m.p. 130°–131°, Mass spectrum: m/e calcd. for C$_{22}$H$_{31}$NO$_3$; 357.2303; measured: 357.2291.

Method C

To a suspension of 12.0 g of 35% potassium hydride in oil, prewashed with hexane, in 100 mL of tetrahydrofuran was added a solution of 9.91 g of 3-benzyl-5-hydroxymethyl-9-methoxy-1,2,3,4,5,6,7,7a-octahydro-4a,7-ethanobenzofuro[3,2-e]isoquinoline (E. Ciganek and B. K. Wong, coassigned pending application, U.S. Ser. No. 774,025) in 50 mL of tetrahydrofuran and the mixture was heated under reflux for 4 hours. Methyl iodide (5.2 g dissolved in 10 mL of tetrahydrofuran) was added to the cooled mixture which was then stirred at room temperature for 18 hours. Addition of 5% hydrochloric acid followed by aqueous ammonium hydroxide solution and extraction with methylene chloride gave 10.47 g of 3-benzyl-9-methoxy-5-methoxymethyl-1,2,3,4,5,6,7,7a-octahydro4a,7-ethanobenzofuro[3,2-e]isoquinoline. NMR spectrum ($\delta$ in CDCl$_3$): 7.5–7.2 (m, 7H); 6.8 (m, 2H); 4.4 (s, 1H); 3.9 (s, 3H), 3.7 (d, J=12 Hz, 1H); 3.5 (d, J=12 H, 1H) and 3.2 (s, 3H), among others.

A mixture of the above product, 80 mL of glacial acetic acid, and 4.0 g of 10% palladium hydroxide on carbon was shaken under 3 atm. of hydrogen at room temperature for 20 hours. The solvent was removed from the filtered solution, the residue was made basic with aqueous sodium hydroxide solution, and the mixture was extracted with methylene chloride. Removal of the solvent gave 8.15 g of crude 9-methoxy-5- methoxymethyl-1,2,3,4,5,6,7,7a-octahydro-4a,7-ethanobenzofuro[3,2-e]isoquinoline whose NMR spectrum showed the major component to be identical to the product obtained by Method B.

To a cooled solution of 5.9 g of the above product in 80 mL of methylene chloride was added 50 mL of a 15% aqueous sodium hydroxide solution followed by 4 mL of propionyl chloride, keeping the temperature below 12°. The mixture was stirred at room temperature for 2 hours, the layers were separated, and the aqueous layer was extracted several times with methylene chloride. Removal of the solvent and chromatography of the residue (silica, elution with 1:2 hexane-ethyl acetate) gave 5.03 g of 9-methoxy-5-methoxymethyl-3-propionyl-1,2,3,4,5,6,7,7a-octahydro-4a,7-ethanobenzofuro[3,2-e]isoquinoline. NMR spectrum (δ in CDCl$_3$); 7.1 (m, 1H); 2.8 (m, 2H); 4.5 (d, J=13 Hz, 1H); 4.4 (s, 1H); 3.9 (s, 3H); 3.4 (s, 3H); 2.9 (d, J=13 Hz) and 1.2 (t, 3H), among others.

To a solution of the above product in 35 mL of tetrahydrofuran was added with cooling 20 mL of a 1M solution of lithium aluminum hydride in tetrahydrofuran. The mixture was heated under reflux for 1 hour, and the excess hydride was decomposed by sequential addition of 0.8 mL of water, 0.8 mL of 15% sodium hydroxide solution, and 2.4 mL of water. Removal of the solvent from the filtered mixture gave 4.45 g of 9-methoxy-5-methoxymethyl-3-n-propyl-1,2,3,4,5,6,7,7a-octahydro-4a,7-ethanobenzofuro[3,2-e]isoquinoline, identical by NMR spectroscopy to the products obtained by Methods A or B. Demethylation as described in Method A gave 5-methoxymethyl-3-n-propyl-1,2,3,4,5,6,7,7a-octahydro-4a,7-ethanobenzofuro[3,2-e]isoquinolin-9-ol.

EXAMPLE 2

5-Ethoxymethyl-3-n-propyl-1,2,3,4,5,6,7,7a-octahydro-4a,7-ethanobenzofuro[3,2-e]isoquinolin-9-ol
($R^1$=CH$_2$CH$_2$CH$_3$; $R^2$, $R^3$, $R^4$=H; $R^8$=C$_2$H$_5$; X=O; a=single bond).

Following the procedure given in Example 1, Method A, but using ethyl iodide in place of methyl iodide in the O-alkylation step, there were obtained in turn;

9-Methoxy-5-ethoxymethyl-3-n-propyl-1,2,5,6,7,7a-hexahydro-4a,7-ethanobenzofuro[3,2-e]isoquinolin-4(3H)-one. NMR spectrum (δ in CDCl$_3$); 6.8 (m, 2H); 6.5 (m, 1H); 4.5 (s, 1H); 3.9 (s, 3H); 1.2 (t, 3H) and 1.0 (t, 3H), among others.

9-Methoxy-5-ethoxymethyl-3-n-propyl-1,2,3,4,5,6,7,7a-octahydro-4a,7-ethanobenzofuro[3,2-e]isoquinoline NMR spectrum (δ in CDCl$_3$); 7.3 (m, 1H); 6.8 (m, 2H); 4.4 (s, 1H); 3.9 (s, 3H); 1.2 (t, 3H) and 0.9 (t, 3H), among others.

5-Ethoxymethyl-3-n-propyl-1,2,3,4,5,6,7,7a-octahydro-4a,7-ethanobenzofuro[3,2-e]isoquinolin-9-ol, m.p. 126°-127°. NMR spectrum (δ in CDCl$_3$); 7.15 (d, J=8 Hz, 1H); 6.8 (d, J=8 Hz, 1H); 6.7 (t, J=8 Hz, 1H); 4.4 (s, 1H); 3.55 (d/d, J=8/5 Hz, 1H); 1.2 (t, 3H) and 0.9 (t, 3H), among others. Mass spectrum: m/e, calcd. for C$_{23}$H$_{33}$NO$_3$; 371.2459; measured 371.2428.

EXAMPLE 3

5-(n-Propoxymethyl)-3-n-propyl-1,2,3,4,5,6,7,7a-octahydro-4a,7-ethanobenzofuro[3,2-e]isoquinolin-9-ol
($R^1$, $R^8$=CH$_2$CH$_2$CH$_3$; $R^2$, $R^3$, $R^4$=H; X=O; a=single bond)

Methanesulfonylchloride (0.65 g) was added slowly to a mixture of 1.53 g of 3-benzyl-5-hydroxymethyl-9-methoxy-1,2,3,4,5,6,7,7a-octahydro-4,7a-ethenobenzofuro[3,2-e]isoquinoline. (E. Ciganek and B. K. Wong, coassigned pending application, U.S. Ser. No. 744,025), 0.58 g of triethylamine and 8 mL of methylene chloride at 0°. After the addition was complete, the mixture was stirred at 0° for 3 hours and then at 25° for 1.5 hours. The mixture was then partitioned between methylene chloride and water. The water layer was extracted with methylene chloride and the combined organic layers were washed with dilute hydrochloric acid, concentrated sodium bicarbonate solution and brine. Removal of the solvent from the dried solution and chromatography on silica gel (elution with 3:1 hexanes:ethyl acetate) gave 0.61 g of 3-benzyl-5-hydroxymethyl-9-methoxy-1,2,3,4,5,6,7,7a-octahydro-4,7a-ethenobenzofuro[3,2-e]isoquinoline methanesulfonate. NMR spectrum (δ in CDCl$_3$): 1.2-1.3 (m, 2H); 1.7-2.0 (m, 2H); 2.1-2.3 (m, 1H); 2.7-3.1 (m, 4H); 2.83 (s, 3H); 3.05-3.25 (m, 1H); 3.55 (d, J=2 Hz, 1H); 3.8, 3.6 (ABq, J=16 Hz, 2H); 3.83 (s, 3H); 4.0-4.1 (m, 1H); 4.4 (d, J=1 Hz, 1H); 5.47 (d, J=2 Hz, 2H); 6.15 (t, J=6.6 Hz, 1H); 6.72 (d, J=2 Hz, 2H); 7.15 (d/d, J=2/6.6 Hz, 1H); 7.2-7.5 (m, 5H).

To a suspension of 0.34 g of sodium hydride in 4 mL of tetrahydrofuran was added 9 mL of n-propyl alcohol. This was followed by 10 mg of 1,4,7,10,13,16-hexaoxacyclooctadecane and 3.35 g of the above methanesulfonate dissolved in 5 mL of tetrahydrofuran. The mixture was heated under reflux for 16 hours, water was added, and the product was extracted into methylene chloride. Removal of the solvent from the dried solution and chromatography of the residue on silica (elution with 3:1 hexanes:ethyl acetate) gave 1.77 g of 3-benzyl-9-methoxy-5-(n-propoxymethyl)-1,2,3,4,5,6,7,7a-octahycdro-4,7a-ethenobenzofuro[3,2-e]isoquinoline. NMR spectrum (δ in CDCl$_3$): 0.9 (t, J=7 Hz, 3H); 1.25 (m, 2H) 1.5 (hex, J=7 Hz, 2H); 1.65-2.0 (m, 2H); 2.1-2.3 (m, 1H); 2.7 (d/d, J=7/18 Hz, 2H); 2.8-3.05 (m, 4H); 3.05-3.33 (m, 4H); 3.6, 3.73 (ABq, J=14 Hz, 2H); 3.8 (s, 3H); 4.35 (d, J=1 Hz, 1H); 5.43 (d, J=7 Hz, 1H); 6.05 (t, J=7 Hz, 1H); 6.67 (d, J=2 Hz, 2H); 7.2 (m, 1H); 7.25-7.5 (m, 5H).

A solution of 0.21 g of the above product in glacial acetic acid was stirred with 0.20 g of 10% palladium on charcoal under hydrogen for 24 hours. The solution was filtered and concentrated, and the residue was partitioned between methylene chloride and aqueous ammonium hydroxide solution. Removal of solvents from a dried solution gave 0.17 g of crude 9-methoxy-5-(n-propoxymethyl-1,2,3,4,5,6,7,7a-octahydro-4,7a-ethanobenzofuro[3,2-e]isoquinoline as an oil. NMR spectrum (δ in CDCl$_3$): 0.87 (t, J=7 Hz, 3H); 1-1.3 (m, 8H); 1.9 (m, 2H); 2.0 (d/t, J=3.5/14 Hz, 1H); 2.40-2.65 (m, 3H); 2.7-2.95 (m, 3H); 3.1-3.35 (m, 3H); 3.43 (t, J=7 Hz, 1H); 3.8 (s, 3H); 4.27 (s, 1H); 6.73 (d, J=3 Hz, 2H); 7.1-7.2 (t, J=3 Hz, 1H).

To a mixture of 0.17 g of the above product, 3 mL of dimethylformamide and 0.07 g of sodium carbonate was added 0.08 g of 1-bromopropane. After stirring at room temperature for 20 hours, the mixture was partitioned between toluene and brine. The water layer was extracted with toluene and the combined organic layers were washed with brine. Removal of the solvent from the dried solution gave 9-methoxy-5-(n-propoxymethyl)-3-n-propyl-1,2,3,4,5,6,7,7a-octahydro-4a,7-ethanobenzofuro[3,2-e]isoquionoline. NMR spectrum (δ in CDCl$_3$): 0.85 (t, J=7 Hz, 6H); 1–1.65 (m, 10H); 1.65–2.00 (m, 2H); 2.0–2.7 (m, 8H); 3.17–3.40 (m, 3H); 3.47 (d/d, J=4/10 Hz, 1H); 3.8 (s, 3H); 4.3 (s, 1H); 6.7 (m, 2H); 7.15 (m, 1H).

Demethylation of the above product as described in Example 1, Method A, chromatography of the crude product on silica (elution with 1:1 ethyl acetatehexane) and crystalline from ethyl acetate gave 5-(n-propoxymethyl)-3-n-propyl-1,2,3,4,5,6,7,7a-octahydro-4a,7-ethanobenzofuro[3,2-e]isoquinolin-9-ol, m.p. 123°–123.5°. NMR spectrum (δ in CDCl$_3$): 0.93 (t, J=7 Hz, 3H); 0.93 (t, J=7 Hz, 3H); 1.2–1.7 (m, 1H); 1.8–1.9 (m, 1H); 1.91 (m, 1H); 2.16–2.55 (m, 6H); 2.55–2.66 (m, 1H); 2.72 (m, 1H); 3.27–3.38 (m, 2H); 3.4 (m, 1H); 3.58 (d/d, J=4.5/7 Hz, 1H); 4.36 (s, 1H); 6.68 (t, J=8 Hz, 1H); 6.78 (d/d, J=2/8, 1H); 7.15 (d, J=8 Hz, 1H). Mass spectrum: m/e calcd. for C$_{24}$H$_{35}$NO$_3$: 385.2615; measured: 385.2589. Anal. calcd. for C$_{24}$H$_{35}$NO$_3$: C, 74.81; H, 9.09; N, 3.64; Found: C, 74.74; H, 9.06; N, 3.52.

EXAMPLE 4

5-(n-Propoxymethyl)-3-n-propyl-1,2,3,4,5,6,7,7a-octahydro-4a,7-ethenobenzofuro[3,2-e]isoquionolin-9-ol (R$^1$, R$^8$=CH$_2$CH$_2$CH$_3$; R$^2$, R$^3$, R$^4$=H; X=O; a=double bond)

A mixture of 0.50 g of 9-methoxy-5-methoxycarbonyl-3-n-propyl-1,3,5,6,7,7a-hexahydro-4,7a-ethenobenzofuro[3,2-e]isoquinolin-2,4-dione (E. Ciganek and B. K. Wong, coassigned pending application U.S. Ser. No. 774,025), and 9 mL of a 1M solution of lithium aluminum hydride in tetrahydrofuran was heated under reflux for 31 hours. Workup as described in Example 1 gave 0.36 g of a product, the NMR spectrum of which showed the product to be 5-hydroxymethyl-9-methoxy-3-n-propyl-1,2,3,4,5,6,7,7a-octahydro-4,7a-ethenobenzofuro[3,2-e]isoquinoline. The product had the following NMR spectrum (δ in CDCl$_3$): 0.80–3.75 (m, 20H); 3.75 (s, 3H); 4.5 (d, J=1 Hz, 1H); 5.43 (d, J=6.6 Hz, 1H); 6.1 (t, J=6.6 Hz, 1H); 6.63 (d, J=3 Hz, 2H); 7.1 (t, J=3 Hz, 1H), among others.

Following the procedure given in Example 3, the above product was converted into its methenesulfonate; NMR spectrum: (δ in CDCl$_3$): 0.9–3.2 (m, 17H); 2.97 (s, 3H); 3.8 (s, 3H); 3.75–3.85 (m, 1H); 4.3 (d/d, J=3/6.7, 1H); 4.4 (s, 1H); 5.53 (d, J=6.7 Hz, 1H); 6.65 (t, s=6.7 Hz, 1H); 6.73 (m, 2H); 7.2 (m, 1H). This product was converted into 9-methoxy-5-(n-propoxymethyl)-3-n-propyl-1,2,3,4,5,6,7,7a-octahydro-4a,7-ethenobenzofuro[3,2-e]isoquinoline as described in Example 3. NMR spectrum (δ in CDCl$_3$): 0.90 (t, J=7 Hz, 3H); 0.97 (t, J=7 Hz, 3H); 1.6 (q, J=7 Hz, 4H); 1.7–1.9 (m, 3H); 2.1–2.35 (m, 1H); 2.4–2.6 (m, 2H); 2.7–3.05 (m, 7H); 3.2–3.4 (m, 2H); 3.5 (m, 1H); 3.8 (s, 3H); 4.4 (s, 1H); 5.5 (d, J=7 Hz, 1H); 6.1 (t, J=7 Hz, 1H); 6.7 (m, 2H) and 7.2 (m, 1H).

The above product was demethylated as described in Example 1, Method A to give 5-(n-propoxymethyl)-3-n-propyl-1,2,3,4,5,6,7,7a-octahydro-4a,7-ethenobenzofuro[3,2-e]isoquinolin-9-ol as an oil. NMR spectrum (δ in CDCl$_3$): 0.87 (t, J=7 Hz, 3H); 0.95 (t, J=7 Hz, 3H); 1.25 (m, 1H); 1.4–1.9 (m, 6H); 2.1–2.3 (m, 1H); 2.4–2.6 (m, 2H); 2.65–3.0 (m, 8H); 3.3–3.4 (m, 2H); 3.5 (m, 1H); 4.35 (d, J=1 Hz, 1H); 5.5 (d, J=7 Hz, 1H); 6.05 (t, J=7 Hz, 1H); 6.6–6.8 (m, 2H) and 7.15 (d, J=7 Hz, 1H).

The fumaric acid salt of the above free base had m.p. 121°–123° after crystallization from methanol. NMR spectrum (δ in CDCl$_3$/DMSO-D6): 0.88 (t, J=7 Hz, 3H); 0.98 (t, J=7Hz, 3H); 1.03 (m, 1H); 1.52 (hex, J=7 Hz, 2H); 1.59–1.75 (m, 2H); 1.76–1.89 (m, 2H); 2.29 (m, 1H); 2.57 (d, J=2 Hz, 2H); 2.65–3.05 (m, 6H); 3.05–3.20 (m, 2H); 3.22–3.40 (m, 4H); 4.34 (s, 1H); 5.49 (d, J=7 Hz, 1H); 6.05 (t, J=7 Hz, 1H); 6.55 (t, J=7 Hz, 1H); 6.62 (d, J=7 Hz, 1H); 6.64 (s, 2H); 7.0 (d, J=7 Hz, 1H).

The mass spectrum was that of the free base; m/e calcd. for C$_{24}$H$_{33}$NO$_3$; 383.2459; measured: 383.2458.

EXAMPLE 5

5-Methylthiomethyl-3-n-propyl-1,2,3,4,5,6,7,7a-4a,7-ethanobenzofuro[3,2-e]isoquinolin-9-ol (R$^1$=CH$_2$CH$_2$CH$_3$; R$^2$, R$^3$, R$^4$=H; R$^8$=CH$_3$; X=S; a=single bond)

To a mixture of 1.01 g of 5-hydroxymethyl-9-methoxy-3-n-propyl-1,2,5,6,7,7a-hexahydro-4a,7-ethanobenzofuro[3,2-e]isoquionolin-4(3H)-one (Example 1, Method A), 10 mL of methylene chloride and 2 mL of triethylamine was added 0.75 mL of methanesulfonyl chloride, keeping the temperature below 0°. After stirring at room temperature for 3 hours, 20 mL of 10% aqueous sodium carbonate solution was added, and the product was extracted into methylene chloride to give 1.69 g of 5-hydroxymethyl-9-methoxy-3-n-propyl-1,2,5,6,7,7a-hexahydro-4a,7-ethanobenzofuro[3,2-e]isoquinolin-4(3H)-one methanesulfonate. NMR (δ in CDCl$_3$): 6.8 (m, 2H); 6.5 (m, 1H); 4.5 (s, 1H); 4.4 (d/d, J=7/10 Hz, 1H); 4.3 (t, J=10 Hz, 1H); 3.9 (s, 3H); 3.0 (s, 3H) and 1.0 (t, 3H), among others.

A mixture of the above methanesulfonate, 1.1 g of potassium methylmercaptide and 7 mL of dimethylformamide was stirred at room temperature for 20 minutes. The mixture was partitioned between toluene and water, and the water layer was extracted with toluene. Removal of the solvent from the dried toluene solution gave 1.11 g of 9-methoxy-5-methylthiomethyl-3-n-propyl-1,2,5,6,7,7a-hexahydro-4a,7-ethanobenzofuro[3,2-e]isoquinolin-4(3H)-one. NMR spectrum (δ in CDCl$_3$): 6.8 (m, 2H); 6.5 (m, 1H); 4.4 (s, 1H); 4.0 (s, 3H); 1.9 (s, 3H) and 0.9 (t, 3H), among others.

A mixture of 0.82 g of the above product, 12 mL of tetrahydrofuran and 1 mL of borane-methyl sulfide complex was heated under reflux for 16 hours. Hydrochloric acid (5 mL) was added to the cooled mixture and the solvents were removed under vacuum. The residue was stirred with 10 mL of acetic acid in an 100°–110° oil bath for 1.5 hours. The solvent was removed, the residue was made basic with aqueous ammonium hydroxide solution and extracted with methylene chloride to give 0.79 g of crude product. It was stirred with toluene and 5% hydrochloric acid, and the resulting precipitate was collected by filtration, washed with water and toluene, and dried. The solid was stirred with aqueous ammonium hydroxide solution and methylene chloride. The aqueous layer was extracted with methylene chloride. Removal of the solvent from the combined, dried organic phases gave 0.60 g of 9-methoxy-5-methylthiomethyl-3-n-propyl-1,2,3,4,5,6,7,7a-octahydro-4a,7-ethanobenzofuro[3,2-e]isoquinoline. NMR spectrum (δ in CDCl$_3$): 7.3 (m, 1H); 6.8 (m, 2H); 4.4 (s, 1H); 3.9 (s, 3H); 2.1 (s, 3H) and 0.9 (t, 3H), among others.

Demethylation of the above product, as described in Example 1, Method A, gave 0.54 g of crude 5-methylthiomethyl-3-n-propyl-1,2,3,4,5,6,7,7a-octahydro-4a,7-ethanobenzofuro[3,2-e]isoquinolin-9-ol. Crystallization from cyclohexane and drying of the crystals at 130° /1 micron gave the pure product, m.p. 152°–153°. NMR spectrum (δ in CDCl₃): 7.18 (d, J=8 Hz; split further, 1H); 6.79 (d, J=8 Hz; split further, 1H); 6.69 (t, J=8 Hz, 1H); 4.36 (d, J=1Hz, 1H); 8.14 (s, 3H) and 0.93 (t, J=7 Hz, 3H), among others. Mass spectrum m/e calcd. for $C_{22}H_{31}NO_2S$; 373.2073; measured 373.2074.

EXAMPLE 6

3-Cyclopropylmethyl-5-methoxymethyl-1,2,3,4,5,6,7,7a-octahydro-4a,7-ethanobenzofuro[3,2-e]isoquinolin-9-ol

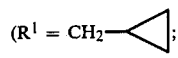

($R^1 = CH_2-$;

$R^2$, $R^3$ $R^4$=H, $R^8$=CH₃; X=O; a=single bond)

3-Cyclopropylmethyl-9-methoxy-5-methoxymethyl-1,2,3,4,5,6,7,7a-octahydro-4a,7-ethanobenzofuro[3,2-e]isoquinoline (synthesized by following the procedures of Example 1, Method A, but starting from 3-cyclopropylmethyl-9-methoxy-5-methoxycarbonyl-1,2,5,6,7,7a-hexahydro-4a,7-ethanobenzofuro[3,2-e]isoquinolin-4-(3H)-one, U.S. Pat. No. 4,477,456) was demethylated as described in Example 1, Method A to give 3-cyclopropylmethyl-5-methoxymethyl-1,2,3,4,5,6,7,7a-octahydro-4a,7-ethano-benzofuro[3,2-e]isoquinolin-9-ol, m.p. 128°–129° after crystallization from ethyl acetate. NMR spectrum (δ in CDCl₃): 7.15 (d, J=8 Hz, 1H); 6.78 (d, J=8 Hz, 1H); 6.68 (t, J=8 Hz, 1H); 4.38 (narrow m, 1H); 3.56 (d/d, J=5/9 Hz, 1H); 3.35 (s, 3H); 3.32 (t, J=9 Hz, 1H); 0.50 (m, 2H); and 0.15 (m, 2H), among others. Mass spectrum: m/e calcd. for $C_{23}H_{31}NO_3$ 369.2302; measured: 369.2318.

EXAMPLE 7

3-Cyclopropylmethyl-5-(3-phenyl-n-propoxymethyl)-1,2,3,4,5,6,7,7a-octahydro-4a,7-ethanolbenzofuro-[3,2-e]isoquinolin-9-ol

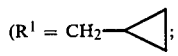

($R^1 = CH_2-$;

$R^2$, $R^3$, $R^4$=H; $R^8$=(CH₂)₃C₆H₅; X=O; a=single bond)

To a solution of 2.06 g of 35% potassium hydride in oil, prewashed with hexane, in 15 mL of tetrahydrofuran was added 0.70 g of 3-cyclopropylmethyl-5-hydroxymethyl-9-methoxy-1,2,5,6,7,7a-hexahydro-4a,7-ethanobenzofuro[3,2-e]isoquinolin-4(3H)-one (synthesized by following the procedures of Example 1, Method A, using 3-cyclopropylmethyl-9-methoxy-5-methoxycarbonyl-1,2,5,6,7,7a-hexahydro-4a,7-ethanobenzofuro[3,2-e]isoquinolin-4(3H)-one, U.S. Pat. No. 4,477,456, as the starting material) and the mixture was heated under reflux for 30 min. Cinnamyl bromide (2 mL) was added to the cooled mixture which was then heated under reflux for 20 minutes. Water and methylene chloride were added, and the aqueous layer was extracted with methylene chloride. Removal of the solvent from the dried organic phases gave 0.84 of 5-cinnamyloxymethyl-3-cyclopropylmethyl-9-methoxy-1,2,5,6,7,7a-hexahydro-4a,7-ethanobenzofuro[3,2-e]isoquinolin-4(3H)-one. NMR spectrum (δ in CDCl₃): 7.1–7.4 (m, 5H); 6.8 (m, 2H); 6.7 (m, 1H); 6.6 (d, J=15 Hz, 1H); 6.3 (d/t, J=15/7 Hz, 1H), 4.4 (s, 1H); 5.8 (m, 2H); 3.9 (s, 3H); 0.5 (m, 2H); and 0.2 (m, 2H), among others.

A mixture of 0.82 g of the above product, 0.05 g of prereduced platinum oxide and 15 mL of ethanol was stirred under hydrogen for 75 minutes. Removal of the solvent from the filtered solution gave 0.81 g of 3-cyclopropylmethyl-9-methoxy-5-(3-phenyl-n-propoxymethyl-1,2,5,6,7,7a-hexahydro-4a,7-ethanobenzofuro-[3,2-e]isoquinolin-4(3H)-one. NMR spectrum (δ in CDCl₃): 7.2 (m, 5H); 6.9 (m, 2H); 6.6 (m, 1H); 4.4 (s, 1H); 3.9 (s, 3H) and 0.5 (m, 2H); and 0.3 (m, 2H) among others.

Reduction of the above product with lithium aluminum hydride using the method described in Example 1, Method A, gave 0.6 g of 3-cyclopropylmethyl-9-methoxy-5-(3-phenyl-n-propoxymethyl)-1,2,3,4,5,6,7,7a-octahydro-4a,7-ethanobenzofuro[3,2-e]isoquinoline. NMR spectrum (δ in CDCl₃): 7.0–7.4 (m, 6H); 6.8 (m, 2H); 4.4 (s, 1H); 3.9 (s, 3H); 0.5 (m, 2H) and 0.1 (m, 2H), among others.

The above product was demethylated as described in Example 1, Method A, to give 3-cyclopropylmethyl-5-(3-phenyl-n-propoxymethyl)-1,2,3,4,5,6,7,7a-octahydro-4a,7-ethanolbenzofuro[3,2-e]isoquinolin-9-ol. The free base was obtained as a glass after chromatography on silica (elution with 2:1 hexane-ethyl acetate). NMR spectrum (δ in CDCl₃): 7.1–7.4 (m, 6H); 6.8 (d, J=8 Hz, 1H); 6.7 (t, J=8 Hz, 1H); 4.4 (s, 1H); 0.5 (m, 2H) and 0.1 (m, 2H), among others. Mass spectrum: m/e calcd. for $C_{31}H_{39}NO_3$: 473.2928; measured: 473.2908.

Table 1 summarizes the compounds prepared in Examples 1 to 7 and compounds that can be prepared by methods described in the specification.

TABLE 1

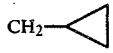

| Ex. No. | R¹ | R² | R³ | R⁴ | R⁸ | X | a | m.p. (°C.) |
|---|---|---|---|---|---|---|---|---|
| 1 | n-C$_3$H$_7$ | H | H | H | CH$_3$ | O | single bond | 130–131 |
| 2 | n-C$_3$H$_7$ | H | H | H | C$_2$H$_5$ | O | single bond | 126–127 |
| 3 | n-C$_3$H$_7$ | H | H | H | n-C$_3$H$_7$ | O | single bond | 123–123.5 |
| 4 | n-C$_3$H$_7$ | H | H | H | n-C$_3$H$_7$ | O | double bond | 121–123 (Fumarate salt) |
| 5 | n-C$_3$H$_7$ | H | H | H | CH$_3$ | S | single bond | 152–153 |
| 6 | CH$_2$—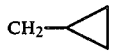 | H | H | H | CH$_3$ | O | single bond | 128–129 |
| 7 | CH$_2$— | H | H | H | (CH$_2$)$_3$C$_6$H$_5$ | O | single bond | Glass |
| 8 | n-C$_3$H$_7$ | CH$_3$ | CH$_3$ | H | CH$_3$ | O | single bond | |
| 9 | n-C$_3$H$_7$ | CH$_3$ | H | H | CH$_3$ | O | single bond | |
| 10 | n-C$_3$H$_7$ | H | H | H | (CH$_2$)$_4$C$_6$H$_5$ | O | single bond | |
| 11 | n-C$_3$H$_7$ | CH$_3$ | CH$_3$ | CH$_3$ | CH$_3$ | O | single bond | |
| 12 | n-C$_3$H$_7$ | H | H | H | C$_6$H$_{11}$ | O | single bond | |
| 13 | n-C$_3$H$_7$ | CH$_3$CO | H | H | CH$_3$ | O | single bond | |
| 14 | n-C$_3$H$_7$ | H | H | CH$_2$C$_6$H$_5$ | CH$_3$ | O | single bond | |
| 15 | n-C$_3$H$_7$ | COC$_6$H$_5$ | C$_2$H$_3$ | (CH$_2$)$_4$C$_6$H$_5$ | 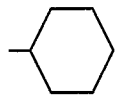 | S | double bond | |
| 16 | CH$_2$C≡CH | C$_6$H$_{13}$CO | i-C$_3$H$_7$ | t-C$_4$H$_9$ | 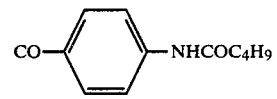 | O | double bond | |
| 17 | CH$_2$C≡CH | C$_{10}$H$_{21}$CO | C$_8$H$_{17}$ | C$_6$H$_{15}$ | C$_7$H$_{15}$ | S | single bond | |
| 18 | —CH$_2$CH=CH$_2$ |  | H | CH=CHCH$_3$ | CH$_2$CH=CH$_2$ | O | single bond | |
| 19 | n-C$_3$H$_7$ | 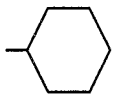 | H | | (CH$_2$)$_3$C$_6$H$_5$ | O | single bond | |
| 20 | n-C$_3$H$_7$ | 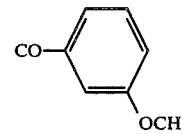 | H | CH$_3$ | CH$_3$ | S | single bond | |

TABLE 1-continued

| Ex. No. | R¹ | R² | R³ | R⁴ | R⁸ | X | a | m.p. (°C.) |
|---|---|---|---|---|---|---|---|---|
| 21 | $CH_2CH=CH_2$ | $CO-C_6H_4-OCHO$ (meta) | H | H | $CH_3$ | S | single bond | |
| 22 | $CH_2CH=CH_2$ | $CO-C_6H_4-NHCH_3$ (para) | H | H | $n-C_3H_7$ | O | single bond | |
| 23 | $CH_2CH=CH_2$ | $CO-C_6H_4-NH_2$ (para) | $CH_3$ | H | $C_2H_5$ | O | double bond | |
| 24 | $n-C_3H_7$ | $CO-C_6H_4-OCOC_2H_5$ (para) | H | H | $CH_3$ | S | double bond | |
| 25 | $n-C_3H_7$ | $CO-C_6H_4-N(CH_3)CHO$ (para) | H | H | $CH_3$ | S | double bond | |
| 26 | $n-C_3H_7$ | $CO-C_6H_4-NHCOCH_3$ (para) | H | H | $CH_3$ | S | double bond | |
| 27 | $CH_2CH=CHCl$ | $CO-C_6H_4-OCHO$ (meta) | H | H | cyclohexyl | O | double bond | |
| 28 | $CH_2C\equiv CH$ | $CH_3$ | $CH_3$ | $CH_3$ | $CH_3$ | O | double bond | |
| 29 | $CH_2CH=C(CH_3)Cl$ | $C_2H_5$ | $C_7H_{15}$ | $C_5H_{11}$ | $CH_2CH=CH_2$ | S | single bond | |
| 30 | $CH_2CH=CH_2$ | $CH_3CO$ | H | H | $CH_3$ | O | single | |
| 31 | $CH_2CH=CHCH_3$ | $CO-C_6H_3(NHCH_3)(OCH_3)$ | $C_2H_5$ | $C_2H_5$ | $C_6H_{11}$ | S | single bond | |

TABLE 1-continued

[Structure: tricyclic compound with R¹-N, OR² on aromatic ring, O bridge, and C(XR⁸)R³R⁴ substituent, with position 'a']

| Ex. No. | R¹ | R² | R³ | R⁴ | R⁸ | X | a | m.p. (°C.) |
|---|---|---|---|---|---|---|---|---|
| 32 | $CH_2CH=CHCl$ | [3,4-dihydroxybenzoyl: CO-C₆H₃(OH)₂] | $C_2H_5$ | H | $CH_3$ | S | single bond | |
| 33 | $\underline{n}$-$C_3H_7$ | [4-hydroxy-3-acetamidobenzoyl: CO-C₆H₃(OH)(NHCOCH₃)] | $CH_3$ | $CH_3$ | $CH_3$ | S | single bond | |
| 34 | $\underline{n}$-$C_3H_7$ | $CH_3$ | H | cyclohexyl | $CH_3$ | O | double bond | |
| 35 | $CH_2CH=CHCl$ | H | $CH_3$ | $C_2H_5$ | $CH_3$ | O | double bond | |
| 36 | $CH_2CH=CHCH_3$ | H | H | H | $CH_3$ | O | double bond | |
| 37 | $\underline{n}$-$C_3H_7$ | H | H | phenyl | $CH_3$ | O | double bond | |

Analgesic and Mu Opioid Antagonist Testing Procedures

A standard procedure for detecting and comparing the analgesic activity of compounds in this series is the phenylquinone writhing test (PQW) modified from E. Seigmund, et al., *Proc. Soc. Exp. Biol. Med.*, 95, 729 (1957).

Test compounds were dissolved in saline or distilled water using dilute lactic acid as needed, or suspended in an aqueous vehicle containing 0.25% by weight of Methocel ® A15C powder, a suspending agent manufactured by Dow Chemical Company and containing 100% methylcellulose. Test compounds were given subcutaneously to fasted (17-21 hours) male white mice (CF₁) 10-20 animals per graded dose. After 5-25 minutes, aqueous (0.01% phenyl p-benzoquinone) phenylquinone, 0.125 mg/kg, was injected intraperitoneally, and 5 minutes later mice were observed for a 10 minute period for the characteristic stretching or writhing syndrome which is indicative of pain produced by phenylquinone. The effective analgesic dose in 50% of the mice (ED₅₀) was calculated by the moving average method of W. R. Thompson, *Bac. Rev.* 11, 115-145 (1947).

A standard procedure useful for detecting the mu receptor opioid antagonist activity of a compound is antagonism of the opioid-induced Straub tail response. Known opioid antagonists such as naloxone and naltrexone prevent the induction of Straub tail response (rigid, elevated tail) in mice by mu agonist agents such as morphine or etonitazene [H. Blumberg, H. B. Dayton and P. S. Wolf, *The Pharmacologist*, 10, 189, (1968)]. This property is the basis of a test in mice for opioid antagonists.

Male CF₁ mice (fasted 17-21 hours), 10-20 per dose, were injected subcutaneously with graded doses of test drug prepared in distilled water or Methocel ® suspending vehicle, and given in a volume of 1 ml per 100 gm of body weight. At an appropriate interval, etonitazene hydrochloride (ETZ) at 0.08 mg/kg was injected intraperitoneally in a volume of 1 ml/100 gm of body weight. After 10 minutes the mice were observed for evidence of a Straub tail condition and scored on a scale of 0 (normal tail) to 5 (most severe, >90° tail elevation). The mean Straub tail score was calculated and linear regression analysis was used to determine the effective dose at which Straub tail severity was reduced by 50% relative to a vehicle-treated control group.

The analgesic and opioid antagonist data are summarized in Table 2.

TABLE 2

OPIOID AGONIST (ANALGESIC) AND ANTAGONIST PROPERTIES

| | ED50, MG/KG, S.C. | |
|---|---|---|
| Ex. No. | ANTAGONISM OF PQ-INDUCED WRITHING IN MICE | ANTAGONISM OF ETZ-INDUCED STRAUB TAIL IN MICE |
| 1 | >81 | 0.01 |
| 2 | >81 | 0.02 |
| 3 | >81 | 0.06 |
| 4 | >81 | 0.15 |
| 5 | >81 | 0.04 |
| 6 | >81 | 0.01 |
| 7 | >81 | 0.13 |
| Naloxone | >81 | 0.016 |
| Naltrexone | >81 | 0.021 |
| Diprenorphine | >81 | 0.006 |
| MR 2266 | >81 | 0.21 |

None of the experimental test compounds demonstrated analgesic activity by antagonizing PQ-induced writhing and are thus characterized as pure antagonist agents.

The foregoing data shows that the compounds of the invention are potent antagonists of mu opioid effects as characterized by their ability to block mu-mediated etonitazene Straub tail response.

Relative Mu and Kappa Opioid Antagonist Property Testing Procedures

The relative mu and kappa antagonist properties of the test compounds were determined by evaluating a compound's ability to counteract the analgesia provided by a fully-effective dose of either a "mu" opioid agonist (morphine sulfate) or a "kappa" opioid agonist (U-50,488H).

Using the standard procedure for evaluating the analgesic activity of compounds (the mouse Phenylquinone Writhing Test (PQW) as described above), a dose of morphine sulfate and a dose of U-50,488H were determined which would provide blockade of the phenylquinone-induced pain response in 90–100% of the animals tested. The relative activity of a compound to antagonize the "mu" (morphine) and "kappa" (U-50,488H) analgesic response were compared and used to provide an index of the kappa antagonist selectivity of each compound.

Male CF$_1$ mice (fasted 17–21 hours), 10–20 per dose, were injected subcutaneously with graded doses of test drug prepared in distilled water or Methocel ® suspending vehicle and given in a volume of 1 ml per 100 gm of body weight. At the appropriate interval, morphine sulfate (2 mg/kg s.c.) or U-50,488H (3 mg/kg s.c.) was injected, followed at 5 to 30 minutes later with a 0.125 mg/kg dose of phenylquinone (phenyl-p-benzoquinone, PQ) injected intraperitoneally. After 5 minutes, mice were observed for 10 minutes for the presence of the characteristic stretching or writhing syndrome which is indicative of the pain produced by the PQ challenge. Animals were scored in an all or none manner; and the presence of a writhing response in an animal treated with an analgesic dose of morphine or U-50,488H was taken as the measure of opioid antagonist effectiveness of the test compound. Quantal antagonist data was determined and linear regression analysis was used to calculate the effective dose at which analgesia was reversed in 50% of the animals tested.

The relative mu and kappa antagonist activity of compounds of the invention are shown below in Table 3.

TABLE 3

MU AND KAPPA ANTAGONIST POTENCIES

| | ED50, MG/KG, S.C. | | |
|---|---|---|---|
| Ex. No. | ANTAGONISM OF MORPHINE ANALGESIA IN PQW TEST (MU ANTAGONIST POTENCY) | ANTAGONISM OF U-50,488H ANALGESIA IN PQW TEST (KAPPA ANTAGONIST POTENCY) | KAPPA SELECTIVITY (MORPHINE/ U-50,488H ANTAGONISM) |
| 1 | .014 [.012; .017] | .004 [.003; .006] | 3.5 X |
| 2 | .024 [.016; .035] | .012 [.008; .020] | 2.0 X |
| 3 | .060 [.032; .111] | .025 [.014; .043] | 2.4 X |
| 4 | .19 [.093; .386] | .05 [.023; .108] | 3.8 X |
| 5 | .10 [.051; .198] | .063 [.036; .111] | 1.6 X |
| 6 | .008 [.005; .013] | .007 [.005; .010] | 1.1 X |
| 7 | .29 [.215; .390] | .24 [.131; .441] | 1.2 X |
| Naloxone | .028 [.021; .037] | .203 [.147; .280] | 0.14 X |
| Naltrexone | .016 [.014; .018] | .067 [.055; .081] | 0.23 X |
| Diprenorphine | .016 [.009; .027] | .086 [.048; 0.154] | 0.19 X |
| MR 2266 | .109 [.079; .151] | .115 [.081; .160] | 0.95 X |

From the test results outlined in Table 3, it can be seen that compounds of this invention have a clearly enhanced degree of kappa selectivity over the standard opioid antagonists naloxone and naltrexone. They are also considerably more kappa-selective than MR 2266, and compound reported to be a relatively selective kappa antagonist. The compound of Example 1 shows 25 times greater kappa selectivity than naloxone, whereas MR 2266 is only 7 times more kappa selective than naloxone. Because of its superior kappa selectivity over naloxone, the more preferred compound of the invention for that purpose is the compound of Example 1.

Utility

The foregoing test results suggest that the compounds of this invention have utility as pure opioid antagonists which are effective at both mu and kappa sites, but have greater selectivity for kappa receptors. In addition, it is expected that compounds of this invention may be more useful than currently available antagonists for treating various forms of shock, stroke, spinal cord trauma, feeding disorders and endocrine dysfunction.

DOSAGE FORMS

Dosage forms (compositions) suitable for administration contain from about 0.1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film-coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams of magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules each containing 100 milligrams of the active ingredient. The capsules are washed in petroleum ether and dried.

Tablets

A large number of tablets are prepared by conventional procedures so that the dosage unit is 100 milligrams of the active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable Composition

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

What is claimed is:

1. A compound having the formula:

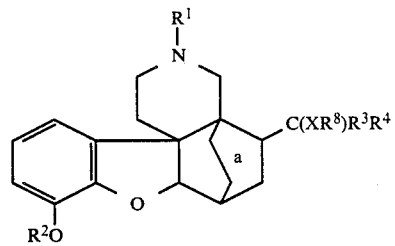

or an acid addition salt thereof, wherein
a is a single or double bond;
$R^1$ is n-propyl or $CH_2R^5$;
$R^2$ is H, alkyl of 1–2 carbons, $C_{2-12}$ acyl an alkanoic acid, or

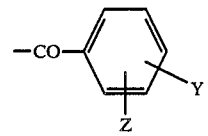

$R^3$ is H or alkyl of 1–8 carbons;
$R^4$ is H, alkyl of 1–8 carbons; alkenyl of 1–8 carbons, cycloalkyl of 3–8 carbons, or $(CH_2)_m C_6H_5$ in which m is 0–4 inclusive;
$R^5$ is $CH=C(R^6)(R^7)$, $C\equiv CH$, or cyclopropyl provided that when $R^5$ is cyclopropyl, then $R^2$, $R^3$ and $R^4$ are independently H, and $R^8$ is $CH_3$ or $(CH_2)_n C_6H_5$ in which n is 3–4;
$R^6$ and $R^7$ independently are H, $CH_3$ or Cl;
$R^8$ is alkyl of 1–8 carbons, alkenyl of 1–8 carbons, cycloalkyl of 3–8 carbons, or $(CH_2)_n C_6H_5$ in which n is 3–4;
X is O or S;
Y and Z independently are H, $OR^9$, $NHR^9$, or $NR^9R^{10}$, provided at least one of Y or Z is $OR^9$, $NHR^9$, or $NR^9R^{10}$;
$R^9$ is H, alkyl of 1–4 carbons, or $COR^{11}$;
$R^{10}$ is alkyl of 1–4 carbons, or $COR^{11}$; and
$R^{11}$ is H or alkyl of 1–4 carbons.

2. A compound of claim 1 wherein $R^1$ is n-propyl or cyclopropylmethyl, provided that when $R^1$ is cyclopropylmethyl, then $R^2$, $R^3$ and $R^4$ are H, and $R^8$ is $CH_3$ or $(CH_2)_n C_6H_5$ in which n=3–4.

3. A compound of claim 1 wherein $R^2$ is H.

4. A compound of claim 1 wherein $R^3$ and $R^4$ are H.

5. A compound of claim 1 wherein $R^8$ is alkyl of 1–3 carbons.

6. A compound of claim 1 wherein X is O.

7. A compound of claim 1 wherein a is a single bond.

8. A compound of claim 2 wherein $R^2$, $R^3$ and $R^4$ are H.

9. A compound of claim 8 wherein $R^8$ is alkyl of 1–3 carbons.

10. A compound of claim 9 wherein X is O.

11. A compound of claim 10 wherein a is a single bond.

12. The compound of claim 1 which is 5-methoxymethyl-3-n-propyl-1,2,3,4,5,6,7,7a-octahydro-4a,7-ethanobenzofuro[3,2-e]isoquinolin-9-ol.

13. The compound of claim 1 which is 3-cyclopropylmethyl-5-methoxymethyl-1,2,3,4,5,6,7,7a-octahydro-4a,7-ethanobenzofuro[3,2-e]isoquinolin-9-ol.

14. A pharmaceutical composition comprising a suitable pharmaceutical carrier and an effective narcotic antagonist or appetite-controlling of at least one compound of claim 1.

15. A pharmaceutical composition comprising a suitable pharmaceutical carrier and an effective narcotic antagonist or appetite-controlling amount of at least one compound of claim 2.

16. A pharmaceutical composition comprising a suitable pharmaceutical carrier and an effective narcotic antagonist or appetite-controlling amount of at least one compound of claim 3.

17. A pharmaceutical composition comprising a suitable pharmaceutical carrier and an effective narcotic antagonist or appetite-controlling amount of at least one compound of claim 4.

18. A pharmaceutical composition comprising a suitable pharmaceutical carrier and an effective narcotic antagonist or appetite-controlling amount of at least one compund of claim 5.

19. A pharmaceutical composition comprising a suitable pharmaceutical carrier and an effective narcotic antagonist or appetite-controlling amount of at least one compound of claim 6.

20. A pharmaceutical composition comprising a suitable pharmaceutical carrier and an effective narcotic antagonist or appetite-controlling amount of at least one compound of claim 7.

21. A pharmaceutical composition comprising a suitable pharmaceutical carrier and an effective narcotic antagonist or appetite-controlling amount of at least one compound of claim 8.

22. A pharmaceutical composition comprising a suitable pharmaceutical carrier and an effective narcotic antagonist or appetite-controlling amount of at least one compound of claim 9.

23. A pharmaceutical composition comprising a suitable pharmaceutical carrier and an effective narcotic antagonist or appetite-controlling amount of at least one compound of claim 10.

24. A pharmaceutical composition comprising a suitable pharmaceutical carrier and an effective narcotic antagonist or appetite-controlling amount of at least one compound of claim 11.

25. A pharmaceutical composition comprising a suitable pharmaceutical carrier and an effective narcotic antagonist or appetite-controlling amount of the compound of claim 12.

26. A pharmaceutical composition comprising a suitable pharmaceutical carrier and an effective narcotic antagonist or appetite-controlling amount of the compound of claim 13.

27. A method for alleviating the effect of an opioid drug, or exerting an appetite-controlling effect in a mammal comprising administering to the mammal an effective amount of at least one compound of claim 1.

28. A method for alleviating the effect of an opioid drug, or exerting an appetite-controlling effect in a mammal comprising administering to the mammal an effective amount of at least one compound of claim 2.

29. A method for alleviating the effect of an opioid drug, or exerting an appetite-controlling effect in a mammal comprising administering to the mammal an effective amount of at least one compound of claim 3.

30. A method for alleviating the effect of an opioid drug, or exerting an appetite-controlling effect in a mammal comprising administering to the mammal an effective amount of at least one compound of claim 4.

31. A method for alleviating the effect of an opioid drug, or exerting an appetite-controlling effect in a mammal comprising administering to the mammal an effective amount of at least one compound of claim 5.

32. A method for alleviating the effect of an opioid drug, or exerting an appetite-controlling effect in a mammal comprising administering to the mammal an effective amount of at least one compound of claim 6.

33. A method for alleviating the effect of an opioid drug, or exerting an appetite-controlling effect in a mammal comprising administering to the mammal an effective amount of at least one compound of claim 7.

34. A method for alleviating the effect of an opioid drug, or exerting an appetite-controlling effect in a mammal comprising administering to the mammal an effective amount of at least one compound of claim 8.

35. A method for alleviating the effect of an opioid drug, or exerting an appetite-controlling effect in a mammal comprising administering to the mammal an effective amount of at least one compound of claim 9.

36. A method for alleviating the effect of an opioid drug, or exerting an appetite-controlling effect in a mammal comprising administering to the mammal an effective amount of at least one compound of claim 10.

37. A method for alleviating the effect of an opioid drug, or exerting an appetite-controlling effect in a mammal comprising administering to the mammal an effective amount of at least one compound of claim 11.

38. A method for alleviating the effect of an opioid drug, or exerting an appetite-controlling effect in a mammal comprising administering to the mammal an effective amount of the compound of claim 12.

39. A method for alleviating the effect of an opioid drug, or exerting an appetite-controlling effect in a mammal comprising administering to the mammal an effective amount of the compound of claim 13.

* * * * *